(12) United States Patent
Alexandre et al.

(10) Patent No.: US 6,610,028 B1
(45) Date of Patent: Aug. 26, 2003

(54) NEEDLESS SYRINGE PROVIDED WITH A PIEZOELECTRIC TRIGGERING SYSTEM

(75) Inventors: Patrick Alexandre, Gray (FR); Bernard Brouquieres, Toulon (FR); Claude Mikler, Dijon (FR); Louis Simonet, La Garde (FR)

(73) Assignee: Crossject, Paris (FR)

(*) Notice: Subject to any disclaimer, the term of this patent is extended or adjusted under 35 U.S.C. 154(b) by 0 days.

(21) Appl. No.: 10/018,356
(22) PCT Filed: Jun. 30, 2000
(86) PCT No.: PCT/FR00/01849
§ 371 (c)(1),
(2), (4) Date: Feb. 4, 2002
(87) PCT Pub. No.: WO01/05452
PCT Pub. Date: Jan. 25, 2001

(30) Foreign Application Priority Data
Jul. 16, 1999 (FR) .............................. 99 09254

(51) Int. Cl.[7] .................................. A61M 5/30
(52) U.S. Cl. ........................ 604/69; 604/68; 604/131
(58) Field of Search ..................... 604/68, 69, 131

(56) References Cited
U.S. PATENT DOCUMENTS
3,802,430 A * 4/1974 Schwebel et al. ............ 604/69
4,089,334 A * 5/1978 Schwebel et al. ............ 604/69
5,693,016 A * 12/1997 Gumaste et al. ............ 604/131

FOREIGN PATENT DOCUMENTS
EP 0 853 952 A1 7/1998

* cited by examiner

Primary Examiner—Michael J. Hayes
Assistant Examiner—Lina R Kontos
(74) Attorney, Agent, or Firm—Oliff & Berridge, PLC

(57) ABSTRACT

The invention concerns the technical field of needleless syringes for injecting an active principle through the skin. More particularly, the invention concerns a needleless syringe provided with a piezoelectric crystal and a triggering device comprising a triggering member and impacting means and, on a triggering device particularly adapted to needleless syringes. The invention is mainly characterized in that the impacting means comprises a latch maintained under elastic stress by being blocked against a stop element and the triggering member is capable of moving the latch to release it, so that it is urged to strike the piezoelectric crystal. Then, the crystal produces an electric arc designed to initiate a pyrotechnic charge whereof the combustion gases will help to expel the active principle contained in the syringe.

14 Claims, 3 Drawing Sheets

NEEDLESS SYRINGE PROVIDED WITH A PIEZOELECTRIC TRIGGERING SYSTEM

The technical field of the invention is that of needleless syringes intended for injection, through the skin, of solid or liquid particles of active principle for therapeutic use.

Specifically, the invention relates, on the one hand, to a needleless syringe functioning on the basis of an initiating device which includes a triggering device associated with a pyrotechnic charge, and, on the other hand, to this triggering device adapted for firing a pyrotechnic charge accommodated in a lightweight object of small size intended to be actuated manually, this object being in particular a needleless syringe.

The solution proposed by the invention recommends the use of a piezoelectric crystal as a central part of the device for triggering the needleless syringe.

It would appear that, in the field of needleless syringes, there is no patent relating to the use of a piezoelectric crystal in the triggering device of such syringes. Mention may be made, however, of European Patent Application EP 0,853,952 which describes an independent initiator casing which can be fitted on needleless syringes and can be used several times. There is merely an allusion made to the fact that this independent initiator casing might possibly include a piezoelectric crystal. In no way, however, does this initiator device form an integral part of the needleless syringe, as underlined by the invention.

By contrast, the use of a piezoelectric crystal for initiating a pyrotechnic charge in objects such as, for example, electrical fuses, blast cartridges or electrical fuse primers is known and is the subject of a number of patents. Reference may be made, inter alia, to French Patent FR 2,665,253 which describes a piezoelectric firing device with resistance wire in a pyrotechnic assembly. This device can be actuated manually by way of a pushbutton with which it is possible to trigger the movement of a weight which is intended to strike the piezoelectric crystal.

The needleless syringes sought by the person skilled in the art must be equipped with a triggering device which can be actuated manually and with which it is possible to do without an activation source which is too energetic or too cumbersome, while at the same time remaining reliable and effective.

The needleless syringe according to the invention meets these requirements.

The subject of the present invention is a needleless syringe provided with an initiating device comprising a triggering device and a pyrotechnic charge, characterized in that the triggering device includes a piezoelectric crystal.

The triggering device advantageously comprises a triggering member connected to a means for impacting the piezoelectric crystal.

The piezoelectric crystal is preferably positioned in the syringe between the impacting means and the pyrotechnic charge to be initiated, and it is inserted in such a way that, during the operation of the syringe, it ensures that the upstream part of the syringe, formed by the triggering member and the impacting means, is leaktight with respect to its downstream part comprising the pyrotechnic charge, the active principle to be injected, and an injection nozzle.

According to a first preferred embodiment of the invention, the impacting means comprises a tongue maintained under elastic stress by being blocked against a stop element, and the triggering member is able to displace said tongue in order to release it, so that it comes to strike the piezoelectric crystal.

The tongue is preferably made of a material having a high degree of elasticity, such as, for example, spring steel or spring bronze.

The tongue advantageously terminates in a weight in order to increase the force of impact on the crystal. This is because the presence of a weight at the end of the tongue will reinforce the action of the lever arm formed by said tongue which is intended to pivot and then strike the crystal at the level of said weight.

The tongue is advantageously integral with the triggering member, so that its displacement before its release is dictated by the movement conferred on the triggering member.

According to a preferred embodiment of the invention, the triggering member is a pushbutton which is intended to be actuated manually and which can slide along an elongate central body, by simple pressure, so as to cause a displacement of the tongue in translation.

The pushbutton is preferably placed at one of the ends of the central body in order to facilitate its actuation, and more especially at the end remote from the injection nozzle.

The central body is preferably hollow and has, on its internal lateral wall, a projection serving as a stop element for the tongue.

The contact surface of the projection against which the weight comes to bear is advantageously plane.

Advantageously, a zone of roughness situated between the pushbutton and the central body makes it possible to increase the frictional forces between these two elements, in the event of the one sliding on the other.

In a preferred manner, the zone of roughness is formed by the mutual engagement of annular protrusions of one of the two elements in grooves provided to receive them in the other element, in such a way as to bring about a minimum level of pressure in order to begin driving the pushbutton home. This precludes any inadvertent triggering caused by insignificant pressure.

The pushbutton preferably has a safety means in the form of a retractable stop element preventing any movement of said button in translation. The other function of this safety means is to protect the end of the syringe through which the active product is to be ejected.

The retractable stop element is advantageously formed by a stopper equipped with a detachable flange, said stopper ensuring protection of the sensitive end of the syringe prior to use, and said flange blocking the pushbutton. A circular line of weakness allows the flange to be separated from the stopper. The flange is rigid and comprises a tab for tearing it off.

According to a second preferred embodiment of the invention, the triggering member is a button which is intended to be actuated manually by rotation about a hollow and elongate central body, in such a way as to cause the rotation of the tongue, said body having, on its internal lateral wall, a projection serving as a stop element for said tongue.

The tongue advantageously terminates in a weight.

The button is preferably placed at one of the ends of the central body in order to facilitate the manual triggering of the syringe.

The rotary button advantageously has a safety means in the form of a retractable ring preventing any rotation of said button.

The retractable ring preferably has a manually accessible tab for tearing off and then removing said ring.

According to a third preferred embodiment of the invention, the impacting means comprises a spring and a weight, and the triggering member is a pushbutton which is intended to be displaced linearly by manual pressure, in such a way as to compress the spring and then release it in order to propel the weight against the piezoelectric crystal.

The spring and the weight are advantageously arranged in an elongate hollow body which serves as a means for guiding them.

The pushbutton preferably has a safety means in the form of a retractable stop element preventing any movement of said button in translation.

The retractable stop element is advantageously formed by a stopper provided with a detachable flange.

In view of what is described for the first preferred embodiment of the invention, the retractable stop element has a dual function: to protect the sensitive end of the syringe and to immobilize the pushbutton.

Finally, the invention concerns a device for triggering a pyrotechnic charge, comprising a triggering member connected to a means for impacting a piezoelectric crystal, said impacting means comprising a tongue maintained under elastic stress by being blocked against a stop element, and the triggering member being able to displace said tongue in order to release it, so that it comes to strike the piezoelectric crystal. The tongue advantageously terminates in a weight in order to increase the force of impact on the crystal. Such a triggering device can, for example, be used for priming grenades. The use of a button which can be actuated by rotation or by pressure is in fact suitable for the priming of grenades to the extent that use of this device is less restrictive than pulling out a pin, especially in a particular situation where the freedom of maneuver of the user is limited, for example when wearing gloves. This device also offers the possibility of priming by means of striking the pushbutton of the grenade hard against an external surface. In general, the triggering device according to the invention, involving the use of a tongue, is adapted to the priming of any type of pyrotechnic charge.

The needleless syringes according to the invention have the advantage of producing a less violent pyrotechnic reaction than that which is observed in the functioning of a percussion primer. Specifically they permit gentle initiation of the pressure-generating composition by way of an electric arc or a spark, and no longer by way of a shock wave.

Moreover, during their triggering and their functioning, they generate an extremely limited sound effect.

Finally, they have the advantage of being placed on the open market without the constraints inherent to devices involving explosives or detonating compositions.

A detailed description of three preferred embodiments of the invention follows below with reference to FIGS. 1 to 6.

Figure 1:
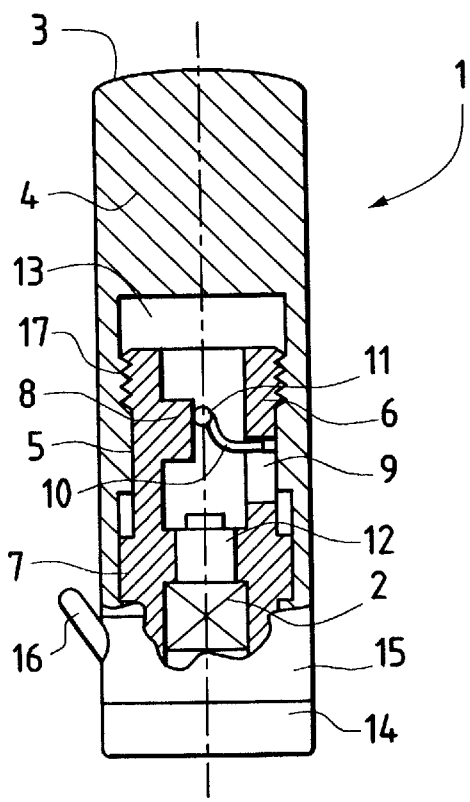
FIG. 1 is a view showing a longitudinal axial section of a needleless syringe according to the invention, which includes a pushbutton and a tongue and which has not yet functioned.

Referring to FIG. 1, according to the first preferred embodiment of the invention, the needleless syringe 1 has an upstream part comprising a triggering device and a downstream part comprising a pyrotechnic charge 2, the active principle in solid or liquid form, an ejection nozzle, and a guide for application to the skin. The triggering device includes a pushbutton 3, an impacting means, and a piezoelectric crystal 12.

The pushbutton 3 has a substantially cylindrical shape and is made up of a solid part 4 continued by a hollow cylindrical part 5 of identical external diameter. This hollow cylindrical part 5 of constant external diameter comprises an internal shoulder making it possible to distinguish between a hollow rear cylinder of large thickness in continuity with a hollow front cylinder of less thickness, the rear cylinder being situated between the solid part 4 and the front cylinder. The rear cylinder has, on its internal lateral wall, a threaded zone. The hollow cylindrical part 5 encloses, along part of its length, a hollow cylindrical body 6 which has a threaded zone on its external lateral wall, said body 6 being continued by a widened cylindrical base 7. The internal lateral wall of the hollow cylindrical body 6 has a projection 8 whose surface is plane, and an opening 9 is made in the wall of said body 6 in a position diametrically opposite that of the plane projection 8. Thus, the internal channel of the hollow cylindrical body 6 opens, at the level of this opening 9, onto the internal lateral wall of the hollow cylindrical part 5 of the pushbutton 3.

Integral with the internal lateral wall of the hollow cylindrical part 5 of the pushbutton 3, a tongue 10 emerges from said opening 9, said tongue 10 terminating at its free end in a weight 11. In the absence of any stress, said tongue 10 is implanted in the internal lateral wall of the hollow cylindrical part 5 in such a way that its natural position corresponds to a position in which the weight 11 is situated well below its point of implantation in the wall.

When the triggering device has not yet functioned, all the components described above are arranged relative to one another in such a way that:

the pushbutton 3 encloses the hollow cylindrical body 6 such that their threaded zones engage in one another and a free space 13 remains between the solid part 4 of the pushbutton 3 and the end of the hollow cylindrical body 6 facing it. It must be emphasized that the term "engage" is appropriate to the situation since the hollow body 6 is not actually screwed into the hollow part 5 of the pushbutton 3. Rather, a series of annular protrusions belonging to the hollow body 6 are engaged in circular grooves hollowed out in the internal lateral wall of the hollow cylindrical part 5 of the pushbutton 3, and vice versa. The aim of this engagement is to create a zone of roughness 17 made up of hard points in such a way as to increase the frictional forces in the event of the pushbutton 3 sliding along the hollow cylindrical body 6, the external lateral wall of the widened base 7 of the hollow cylindrical body 6 is in contact with the internal lateral wall of the front cylinder of the hollow cylindrical part 5 of the pushbutton 3, the end of the front cylinder is turned back on the base 7 in such a way as to ensure that the pushbutton 3 cannot be easily removed from the syringe 1, the tongue 10 is elastically deformed by rotation about an axis passing through the point of contact between said tongue 10 and the internal lateral wall of the cylindrical part 5 on which it is implanted, this axis being simultaneously perpendicular to the axis of the tongue 10 and to the axis of the hollow cylindrical body 6. After it has been deformed elastically, said tongue 10 is blocked against the plane projection 8, at the level of the weight 11, the tongue 10 under stress emerges from the opening 9, being in contact with the edge of said opening 9 nearest to the solid part 4 of the pushbutton 3.

A cylindrical pyrotechnic charge 2 is fixed in the hollow cylindrical body 6 in such a way that its external lateral wall remains in contact with the internal lateral wall of said body 6. A piezoelectric crystal 12 is placed between the pyrotechnic charge 2 and the stressed tongue 10, being in contact with one of the two circular faces of said charge 2. The syringe 1 has a safety means in the form of a retractable stop element formed by a stopper 14 which is provided with a detachable rigid flange 15, having the same diameter as the external diameter of the pushbutton 3. The stopper 14 of cylindrical shape comes to engage around the sensitive end of the syringe 1 through which the active principle will be expelled.

The flange 15, which is of cylindrical shape, is integral with the stopper 14 and is blocked between said stopper 14 and the free end of the hollow cylindrical part 5 of the pushbutton 3.

A zone of preliminary cutting, in the form of a circular groove, is formed between the flange 15 and the stopper 14, and a tab 16 fixed to said flange 15 can be easily taken hold of by the user in order to help detach the flange 15.

The functioning of this preferred syringe variant according to the invention involves the following steps.

The user takes hold of the tab 16 and acts in such a way as to separate the flange 15 and the stopper 14 along the circular line of preliminary cutting. Once the flange 15 has been removed, the protective stopper 14 is in turn removed and the syringe 1 is thus unlocked.

Figure 2:
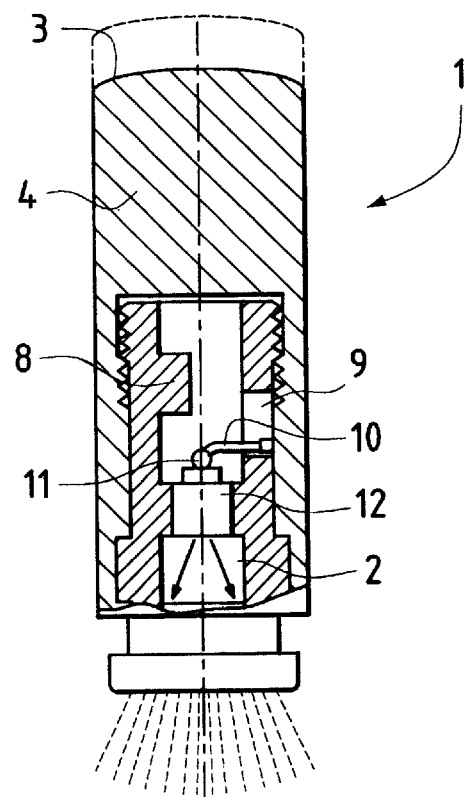
FIG. 2 is a view showing a longitudinal axial section of the syringe from FIG. 1, after it has functioned.

The downstream part of the syringe 1 is placed in contact with the skin of the patient to be treated. The user then exerts a manual pressure on the pushbutton 3 in the area of its solid part 4, in such a way as to drive it home. To do this, he has to apply a force to overcome the frictional forces induced by the zone of roughness 17. When the pushbutton 3 begins to slide along the hollow cylindrical body 6, it brings about a linear displacement of the stressed tongue 10 integral with it. The end of said tongue 10 terminating in the weight 11 then slides along the projection 8 at the same speed as the displacement of the pushbutton 3. Referring to FIG. 2, by accentuating the pressure on the pushbutton 3, the end of the tongue 10 arrives at the end of the projection 8 and then, when the linear displacement continues, pivots abruptly to recover its natural unstressed position.

This abrupt pivoting accelerates the weight 11 which strikes at high speed against the piezoelectric crystal 12 placed in contact with the pyrotechnic charge 2. The crystal 12 produces an electric arc which initiates the pyrotechnic charge 2, the combustion of which will generate gases which will help eject the active principle through the skin of the patient. The maximum displacement of the pushbutton 3 corresponds to the abutment of the internal shoulder of the hollow cylindrical part 5 against the widened base 7 of the hollow cylindrical body 6.

Figure 3:
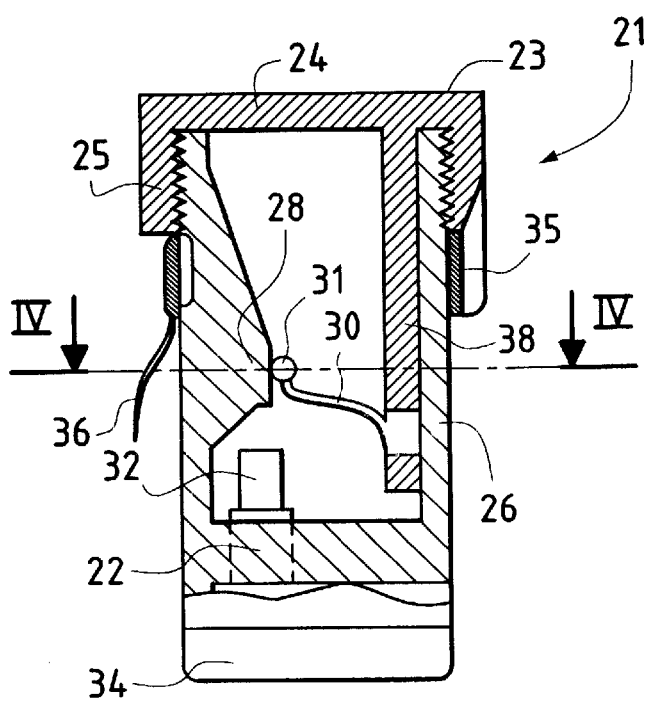
FIG. 3 is a view showing a longitudinal axial section, on the plane III—III, of a syringe according to the invention which includes a rotary button and a tongue and which has not yet functioned.
Figure 4:
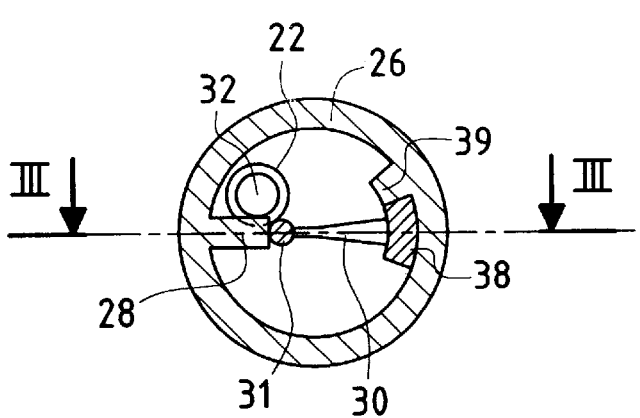
FIG. 4 is a view showing a transverse axial section, on the plane IV—IV, of the syringe in FIG. 3.
Figure 5:
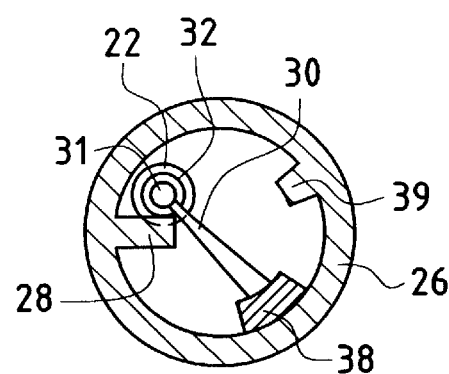
FIG. 5 is the same view as in FIG. 4, but for a syringe which has functioned.

Referring to FIGS. 3, 4 and 5, according to the second preferred embodiment of the invention, the syringe 21 has an upstream part comprising a triggering device and a pyrotechnic charge 22, the active principle in solid or liquid form, and a downstream part encompassing an ejection nozzle and a guide for application to the skin. The triggering device includes a button 23 which can be actuated by rotation, an impacting means, and a piezoelectric crystal 32. The button 23 consists of a cylindrical lateral wall 25, threaded on its internal surface, and of a plane circular face 24 closing off one of the two ends of said lateral wall 25.

Moreover, the button 23 has the particular feature of having a protuberance 38 in the form of a cylinder portion defined by a constant length and which would result from cutting a complete cylinder along two radial planes. This protuberance 38, whose shape could be likened to that of an incurved rectangular parallelepiped, is situated on the plane circular surface 24 of the button 23 in a position in which the generatrices of this protuberance 38 are parallel to the axis of rotation of said circular surface 24, and in such a way that said protuberance 38 is arranged concentrically with respect to the cylindrical lateral wall 25 of said button 23. This button 23 is screwed around a hollow cylindrical body 26 of constant external diameter and having a threaded zone situated at one of its ends and on its external surface. The internal wall of the hollow cylindrical body 26 has two projections. One 39 of elongate shape, which emerges only slightly and whose length is similar to that of the protuberance 38, is arranged parallel to the axis of the hollow cylindrical body 26. The other 28 is more distinct than the first 39, but its height of emergence in the internal channel of the hollow cylindrical body 26 is still smaller than the radius of said internal channel.

The protuberance 38 of the button 23 has, in proximity to its free end, a tongue 30 which terminates in a weight 31.

In the absence of any stress, said tongue 30 is implanted in the protuberance 38 in such a way that its natural position corresponds to a position in which the weight 31 is situated well below its point of implantation in the protuberance 38.

When the triggering device has not yet functioned, all the components described above are arranged in relation to one another such that:

the button 23 is screwed around the threaded end of the hollow cylindrical body 26, and the protuberance 38 is placed inside said cylindrical body 26 and in contact with its internal lateral wall since the curvature of said protuberance 38 respects that of said internal wall, the protuberance 38 integral with the button 23 is in abutment against the projection 39 the less advanced but substantially of the same length, in such a way as to block one of the two possible directions of rotation of said button 23, the tongue 30 which is made of spring steel is deformed elastically by rotation about an axis passing through the point of contact between said tongue 30 and the protuberance 38 which bears it, this axis being simultaneously perpendicular to the axis of the tongue 30 and to the axis of the hollow cylindrical body 26. After it has been deformed elastically, said tongue is blocked against the more advanced projection 28 of the hollow cylindrical body 26.

A cylindrical pyrotechnic charge 22 is fixed in the hollow cylindrical body 26 in such a way that its external lateral wall remains in contact with the internal lateral wall of said body 26.

A piezoelectric crystal 32 is placed between the pyrotechnic charge 22 and the stressed tongue 30, in contact with one of the two circular faces of said charge 22.

The syringe 21 has a safety means in the form of a retractable ring 35 with safety tab enclosing the button 23 and preventing any rotation of the latter. A tab 36 fixed to said ring 35 can be easily taken hold of by the user in order to help tear off the ring 35. A stopper 34 engages around the sensitive end of the syringe 21 through which the active principle will be expelled.

The functioning of this preferred syringe variant according to the invention is divided up into the following steps.

The user takes hold of the tab 36 and acts in such a way as to tear the ring 35 for the purpose of removing it and thus unlocking the syringe 21. The downstream part of the syringe 21 is placed in contact with the skin of the patient to be treated. The user begins to turn the button 23 in the only direction permitted by the projection 39 serving as a stop element for the protuberance 38. The rotation of the button 23 causes the rotation of the protuberance 38 and thus that of the end of the tongue 30 terminating in the weight 31 which bears against the projection 28.

By accentuating the rotation of the button 23, the end of the tongue 30 ends up leaving the projection 28 against which it was bearing. The tongue 30 then pivots abruptly to recover its natural unstressed position. This abrupt pivoting accelerates the weight 31 which comes to strike at high speed against the piezoelectric crystal 32 placed in contact with the pyrotechnic charge 22. The crystal 32 produces an electric arc which initiates the pyrotechnic charge 22, the combustion of which will generate gases which will help eject the active principle through the skin of the patient.

Figure 6:
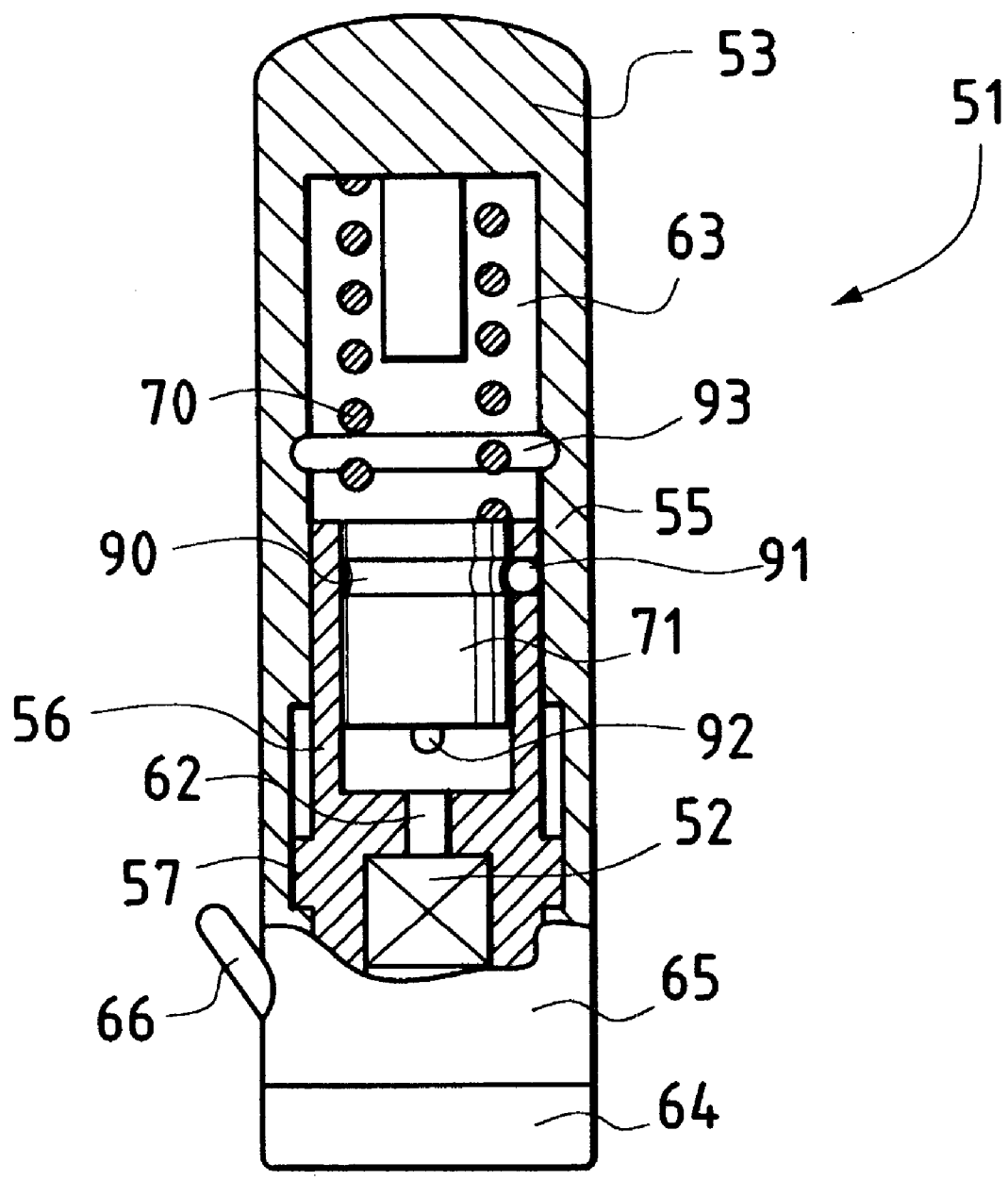
FIG. 6 is a view showing a longitudinal axial section of a needleless syringe according to the invention, which includes a pushbutton, a spring and a weight, and which has not yet functioned.

Referring to FIG. 6, according to the third preferred embodiment of the invention, the syringe 51 has an upstream part comprising a triggering device and a pyrotechnic charge 52, the active principle in solid or liquid form, and a downstream part encompassing an ejection nozzle and a guide for application to the skin. The triggering device includes a pushbutton 53, an impacting means and a piezoelectric crystal 62. The pushbutton 53 is made up of a cylindrical lateral wall 55 of constant external diameter and with a closed end of rounded shape. Said wall 55 includes an internal shoulder making it possible to distinguish a rear cylinder of large thickness in continuity with a front cylinder of less thickness, the rear cylinder being located between the rounded end of the pushbutton 53 and the front cylinder. This lateral wall 55 encloses, over part of its length, a hollow cylindrical body 56 of constant external diameter and with a widened cylindrical base 57. Said hollow body 57 has a constriction with which it is possible to divide the internal channel of said body into three zones, each one continuing on from the other, and each having a constant diameter: an upstream zone, which is the nearest to the rounded end of the pushbutton 53 and in which is accommodated a cylindrical weight 71 having a circular groove 90 at its periphery; an intermediate zone of reduced diameter constituting the zone of constriction in which a piezoelectric crystal 62 is accommodated; and a downstream zone which is of increased diameter relative to that of the intermediate zone and in which a pyrotechnic charge 52 of substantially cylindrical shape is accommodated. The external lateral walls of the piezoelectric crystal 62 and of the pyrotechnic charge 52 are in contact with the internal wall of the hollow body 56 which encloses them, at the level of the intermediate zone and of the downstream zone, respectively. Moreover, said crystal 62 and said charge 52 are in contact with one another.

Likewise, the external lateral wall of the weight 71 is in contact with the internal lateral wall of the hollow body 56 which accommodates it in the area of the upstream zone, except however for the part of said weight 71 formed by the circular groove 90. The weight 71 has two plane circular faces, one of which has a central protrusion 92 which is perpendicular to it. In the area of the upstream zone, the hollow body 56 has at least one hole which allows the internal channel of said hollow body 56 to communicate with the internal lateral wall 55 of the pushbutton 53, said wall being in contact with the external lateral wall of the hollow body 56. Each hole is occupied by a ball 91 whose diameter is greater than the thickness of the wall of the hollow body 56 in which the hole has been made, said ball 91 being wedged between the internal lateral wall 55 of the pushbutton 53 and the circular groove 90 of the weight 71. Advantageously, the hollow body 56 has a plurality of holes which are aligned and regularly spaced at its periphery, each one accommodating a ball 91, in such a way as to better distribute the forces exerted on the weight 71.

This ball 91 makes it possible to block the weight 71 in the hollow body 56 in such a way that the plane circular face of said weight 71 not having the protrusion 92 is flush with the end of the hollow cylindrical body 56 in which it is accommodated. In this way, a free space is left between the plane circular face of the weight 71 having the protrusion 92 and the piezoelectric crystal 62. The pushbutton 53 encloses the hollow cylindrical body 56 in such a way as to form a free space 63 in the rear cylinder of the cylindrical lateral wall 55 of said pushbutton 53, said space 63 being delimited by the internal face of the rounded end of the pushbutton 53 and the plane circular surface comprising the plane circular face of the flush weight 71 not having the protrusion 92 and the circular band of the hollow cylindrical body 56 which the face of said weight 71 is level with. In this space 63, the internal lateral wall of the pushbutton 53 is hollowed out with a circular groove 93 which allows it, at this location, to widen its diameter, and a spring 70 comes into abutment, on the one hand, against the internal face of the rounded end of the pushbutton 53 and, on the other hand, against the plane circular face of the weight 71 remote from that having the protrusion 92. The syringe 51 has a safety means in the form of a retractable stop element formed by a stopper 64 equipped with a detachable rigid flange 65 which has the same diameter as the external diameter of the pushbutton 53. The stopper 64 of cylindrical shape engages around the sensitive end of the syringe 51 through which the active principle will be expelled. The flange 65 which is of cylindrical shape is integral with the stopper 64 and is blocked between said stopper 64 and the free end of the hollow cylindrical part 55 of the pushbutton 53.

A zone of preliminary cutting, in the form of a circular groove, is formed between the flange 65 and the stopper 64, and a tab 66 fixed to said flange 65 can be easily taken hold of by the user in order to help detach the flange 65.

The functioning of this preferred syringe variant according to the invention involves the following steps.

The user takes hold of the tab 66 and acts in such a way as to separate the flange 65 from the stopper 64 along the circular line of preliminary cutting. Once the flange 65 has been removed, the protective stopper 64 is in turn removed and the syringe 51 is thus unlocked.

The downstream part of the syringe 51 is placed in contact with the skin of the patient to be treated. The user then exerts a manual pressure on the pushbutton 53 which moves down, sliding about the hollow cylindrical body 56. The spring 70 is compressed against the weight 71 blocked by the balls 91, while the circular groove 93 hollowed out in the internal lateral wall 55 of the pushbutton 53 approaches said ball 91. By accentuating the pressure, said groove 93 reaches the level of the ball 91 which then disengages into the new space offered by the groove 93. The weight 71 which is no longer blocked by the balls 91 but which is subjected to the pressure of the compressed spring 70 is violently propelled toward the piezoelectric crystal 62. The protrusion 92 on the weight 71 comes to strike against said crystal 62 which reacts by producing an electric arc.

The pyrotechnic charge 52 is then initiated in combustion and the gases produced will help to expel the active principle.

The maximum displacement of the pushbutton 53 corresponds to the abutment of the internal shoulder of the cylindrical lateral wall 55 against the widened base 57 of the hollow cylindrical body 56.

What is claimed is:

1. A needleless syringe provided with an initiating device comprising a triggering device and a pyrotechnic charge (2, 22, 52), said triggering device including a piezoelectric crystal (12, 32, 62) and a triggering member (3, 23, 53) connected to a means for impacting said crystal (12, 32, 62), characterized in that the impacting means comprises a tongue (10, 30) maintained under elastic stress by being blocked against a stop element (8, 28), and the triggering member (3, 23) is able to displace said tongue (10, 30) in order to release it, so that it comes to strike the piezoelectric crystal (12, 32).

2. The needleless syringe as claimed in claim 1, characterized in that the tongue (10, 30) terminates in a weight (11, 31) in order to increase the force of impact on the crystal (12, 32).

3. The needleless syringe as claimed in claim 1, characterized in that the tongue (10, 30) is integral with the triggering member (3, 23) so that its displacement before its release is dictated by the movement conferred on the triggering member (3, 23).

4. The needleless syringe as claimed in claim 3, characterized in that the triggering member (3) is a pushbutton which is intended to be actuated manually and which can slide along an elongate central body (6), by simple pressure, so as to cause a displacement of the tongue (10) in translation.

5. The needleless syringe as claimed in claim 4, characterized in that the central body (6) is hollow and has, on its internal lateral wall, a projection (8) serving as a stop element for the tongue (10).

6. The needleless syringe as claimed in claim 4, characterized in that a zone of roughness (17) situated between the pushbutton (3) and the central body (6) makes it possible to increase the frictional forces between these two elements, in the event of the one sliding on the other.

7. The needleless syringe as claimed in claim 3, characterized in that the triggering member (23) is a button which is intended to be actuated manually by rotation about a hollow and elongate central body (26), in such a way as to cause the rotation of the tongue (30), said body (26) having, on its internal lateral wall, a projection (28) serving as a stop element for said tongue (30).

8. The needleless syringe as claimed in claim 4, characterized in that the button (3, 23) is placed at one of the ends of the central body (6, 26).

9. The needleless syringe as claimed in claim 7, characterized in that the button (23) has a safety means in the form of a retractable ring (35) preventing any rotation of said button (23).

10. The needleless syringe as claimed in claim 1, characterized in that the impacting means comprises a spring (70) and a weight (71), and the triggering member (53) is a pushbutton which is intended to be displaced linearly by manual pressure, in such a way as to compress the spring (70) and then release it in order to propel the weight (71) against the piezoelectric crystal (62).

11. The needleless syringe as claimed in either of claims 4 and 10, characterized in that the pushbutton (3, 53) has a safety means in the form of a retractable stop element preventing any movement of said button (3, 53) in translation.

12. The needleless syringe as claimed in claim 11, characterized in that the retractable stop element is formed by a stopper (14, 64) provided with a detachable flange (15, 65).

13. A triggering device intended to form the needleless syringe (1, 21) as claimed in claim 1, characterized in that it comprises a triggering member (3, 23) connected to a means for impacting a piezoelectric crystal (12, 32), said impacting means comprising a tongue (10, 30) maintained under elastic stress by being blocked against a stop element (8, 28), and the triggering member (3, 23) being able to displace said tongue (10, 30) in order to release it, so that it comes to strike the piezoelectric crystal (12, 32).

14. The triggering device as claimed in claim 13, characterized in that the tongue (10, 30) terminates in a weight (11, 31) in order to increase the force of impact on the crystal (12, 32).

* * * * *